United States Patent
Anglade et al.

(12) 
(10) Patent No.: US 6,403,333 B1
(45) Date of Patent: Jun. 11, 2002

(54) METHOD FOR DETERMINING THE EXISTENCE OF A BIOLOGICAL ACTIVITY OF MICROORGANISMS

(75) Inventors: Jean-Yves Anglade, Marseille; Nathalie Barsotti, Six Fours; Michel Biosrayon, Le Beausset; Corinne Denunzio Dejugnac, La Seyne/mer; Jean Le Petit, Allanch; Robert Matheron, Marseille; Alain Scarpitta, Toulon, all of (FR)

(73) Assignee: Etat Francais represente parlle Delegue General pour l'Armement, Arcuiel (FR)

( * ) Notice: Subject to any disclaimer, the term of this patent is extended or adjusted under 35 U.S.C. 154(b) by 0 days.

(21) Appl. No.: 09/719,683

(22) PCT Filed: Apr. 17, 2000

(86) PCT No.: PCT/FR00/00988

§ 371 (c)(1),
(2), (4) Date: Feb. 8, 2001

(87) PCT Pub. No.: WO00/63428

PCT Pub. Date: Oct. 26, 2000

(30) Foreign Application Priority Data

Apr. 15, 1999 (FR) .............................. 99 04731

(51) Int. Cl.[7] .......................... C12Q 1/04; C12Q 1/02; G01N 27/00; G01N 27/02
(52) U.S. Cl. .............................. 435/34; 435/29; 435/4; 422/82.01; 422/82.02; 422/50
(58) Field of Search .................. 435/34, 29; 422/82.01, 422/82.02, 50

(56) References Cited

U.S. PATENT DOCUMENTS 4,321,322 A    3/1982   Ahnell ..................... 435/34
4,326,934 A  * 4/1982   Pohl
4,898,816 A    2/1990   Turner et al. ................ 435/34
5,182,193 A  * 1/1993   Mishima et al.
5,814,916 A  * 9/1998   Dejugnac et al.
5,824,494 A   10/1998   Feldberg ..................... 435/40

FOREIGN PATENT DOCUMENTS

EP    0 184 260    6/1986
EP    0 219 247    4/1987
EP    0 221 663    5/1987
EP    0 238 322    9/1987
EP    0 352 138    1/1990
EP    0 543 090    5/1993
JP    11-127891    5/1999

OTHER PUBLICATIONS

Hamilton, W. A. et al., "Effects of High Electric Fields on Microorganisms. II. Mechanism of Action of the Lethal Effect," Biochimica et Biophysica Acta, vol. 148, pp. 789–800, 1967.

* cited by examiner

Primary Examiner—Ralph Gitomer
Assistant Examiner—Mahreen Chaudhry
(74) Attorney, Agent, or Firm—Oliff & Berridge, PLC

(57) ABSTRACT

The invention relates to a method enabling the existence of a biological activity of microorganisms to be determined quickly by applying an electric field. The inventive method includes the following: the microorganisms are placed in a suspension in a dielectric oil, an electric field is applied to said suspension and variations in the strength of the leakage current induced as a function of the applied electric field are measured. The device according to the invention comprises a container which is fitted with electrodes (2), whereby the suspension (3) of microorganisms in a dielectric oil is placed therein, in addition to means for generating an electric field between two or several electrodes, measuring means and means for recording the induced leakage current.

10 Claims, 5 Drawing Sheets

METHOD FOR DETERMINING THE EXISTENCE OF A BIOLOGICAL ACTIVITY OF MICROORGANISMS

BACKGROUND OF THE INVENTION

1. Field of the Invention

The present invention relates to a method for determining whether microorganisms have retained biological activity.

The strength of the leakage current generated by the electrical field applied to a microorganism suspension in a dielectric oil gives information on whether or not biological activity is present. When followed by a microorganism collection and counting stage, the method can be used to determine the viability of the microorganisms after an electrical field has been applied.

Simple and rapid determination of the biological activity of microorganisms is essential in many fields such as pollution control, quality assurance, and clinical analysis. In research and in the food and agricultural industry, microorganisms such as bacteria and yeast are tools in increasingly widespread use. The use and effectiveness of the various biochemical processes involved depend on the viability of these microorganisms.

This being the goal, the standard technique consists of culturing a sample under specific conditions in an appropriate medium of the agar—agar type. If the items sampled and observed visually or under the microscope and counted are shown actually to reproduce, it may be determined that they are biologically active. In this case, the original strain is declared to be living. If not, it is concluded to be biologically inactive.

This method has a number of drawbacks, particularly the time required for the result to be obtained. In the best case, 18 hours are needed for visible colonies to form.

2. Description of the Related Field

EP Patent 0543090 proposes an analytical method based on direct measurement of the metabolic activity of bacteria, using a bioelectrochemical cell. Several aspects of the bioelectrochemical detection system are described in EP Patent 0221663 relating to a method and an instrument for measuring microbial activity in a bioelectrochemical cell, EP 0219247 relating to the bioelectrochemical cell and its electrodes, EP 0238322 relating to bioelectrochemical mediators, and EP 0352138 relating to improved electrodes used in bioelectrochemical cells. Some of these methods involve a step prior to analysis in which the bacteria are concentrated on a filter, an essential element of the device. Others use an electrode with a special configuration and special composition, made of expensive precious metals or porous carbon.

Whatever the systems described in these patents, the use of a chemical mediator is essential. This mediator is an organic compound such as 1,4-benzoquinone, which is dissolved in the medium and serves for transferring electrons between the electrodes and the microorganisms. When it contacts bacteria, it generates a response which is detected and measured by the measuring electrodes. The responses measured vary greatly depending on the mediator, its concentration, and its degree of oxidation, making it difficult to interpret and compare the results. Moreover, if any contaminants or elements able to exchange electrons with the mediator are present, numerous artefacts result. Finally, the presence of the mediator and a filter make it difficult to recover the microorganisms studied at a later time.

When a bioelectrochemical cell is used, the microorganisms are subjected to electrical fields in an aqueous medium, particularly in a buffer at the specified ionic concentrations. The high-frequency alternating currents produce alternating or rotating electrical fields. Such conditions do not allow voltages higher than a few volts to be applied for more than a few seconds. When direct current is used, the electrical voltage produced by capacitor discharge is always transient or pulsed. It can be kept at a high value, several kilovolts, for only very short times, less than one second, so that discontinuous or stepped measurements cannot be performed.

SUMMARY OF THE INVENTION

The goal of the invention is to overcome the above drawbacks by offering a rapid method for determining the state of a microorganism culture, adaptable to various microorganism species.

Another goal of the present invention is to furnish a device designed for simple and inexpensive implementation of the above method. Another goal is to enable the microorganisms studied to be recovered once an electrical field according to the method of the invention has been applied.

For this purpose, the invention relates to a method for determining the existence of microorganism biological activity by applying an electrical field, characterized by including application of an electrical field to a dielectric medium comprised of microorganisms suspended in a dielectric oil and measuring a characteristic leakage current when the microorganisms are alive.

For making the cell suspension, the microorganisms are first removed from the surface of an agar culture medium then placed in a dielectric oil. The dielectric oil can be a mixture of oils or a mineral or organic oil, preferably a silicone oil. The microorganism/dielectric oil mixture can be homogenized with an ultrasound probe.

The method according to the invention consists of gradually applying an electrical field to the dielectric suspension from the value zero to the maximum selected value. Application of the electrical field creates a leakage current in the medium containing the microorganisms and the dielectric oil. When the microorganisms are alive, the variations in leakage current strength as a function of the electrical field applied are characteristic and indicate whether biological activity is present. Whatever the stress resulting from application of the electrical field, a peak characteristic of the viability of the microorganisms studied appears. When the microorganisms are dead, on the other hand, the change in strength observed is a constant function of the electrical field appied.

The invention also relates to a device for determining whether microorganisms are biologically active, characterized by comprising a container equipped with electrodes in which the microorganism suspension is placed in a dielectric oil, means for generating an electrical field between two or more electrodes, measuring means, and means for recording the leakage current induced. The container in which the microorganism suspension is introduced is equipped with metal electrodes.

According to another embodiment of the invention, the container in which said suspension is introduced is comprised of an insulating plate provided with an inter-electrode space. Preferably, the voltage of the electrical current between the electrodes varies from 0 to 250 volts per millimeter.

Application of the electrical field, according to the method of the invention, may be followed by transfer to an aqueous medium, followed by counting. This application of the method is a simple and effective means of selecting the microorganisms that survive the electrical field.

BRIEF DESCRIPTION OF THE DRAWINGS

The characteristics and advantages of the invention will emerge from the non-limiting description of the examples below.

DETAILED DESCRIPTION OF PREFERRED EMBODIMENTS

EXAMPLE 1

When the microorganisms studied come from an agar culture medium, they are scraped off the surface and placed in an Eppendorf microtube containing 1 ml of dielectric oil of the silicone oil type. An ultrasound probe is placed in the microtube. Ultrasound waves with a power of 25 W and a frequency of 20 kHz are applied to the mixture for 30 seconds alternating with 2 to 3 rest phases lasting 5 seconds each, in order to obtain a homogeneous suspension; any cell aggregates and agar present are centrifuged off at 4000 rpm for 30 seconds at 4° C. The homogenous suspension is then introduced into one of the containers shown in FIGS. 1 and 2. The space between electrodes 2 is 1.8 mm for the device shown in FIG. 1 and 3 mm for the device in FIG. 2. A DC voltage varying gradually from 0 to 250 volts per mm is furnished by a generator and applied gradually to the suspension. In parallel, an ammeter records the leakage current induced.

According to the shape of the curve representing the change in the strength of the leakage current 1 in microamperes as a function of the voltage V of the applied electrical field between electrodes 2, it can be immediately and readily determined whether the microorganisms are alive or dead.

Figure 1:
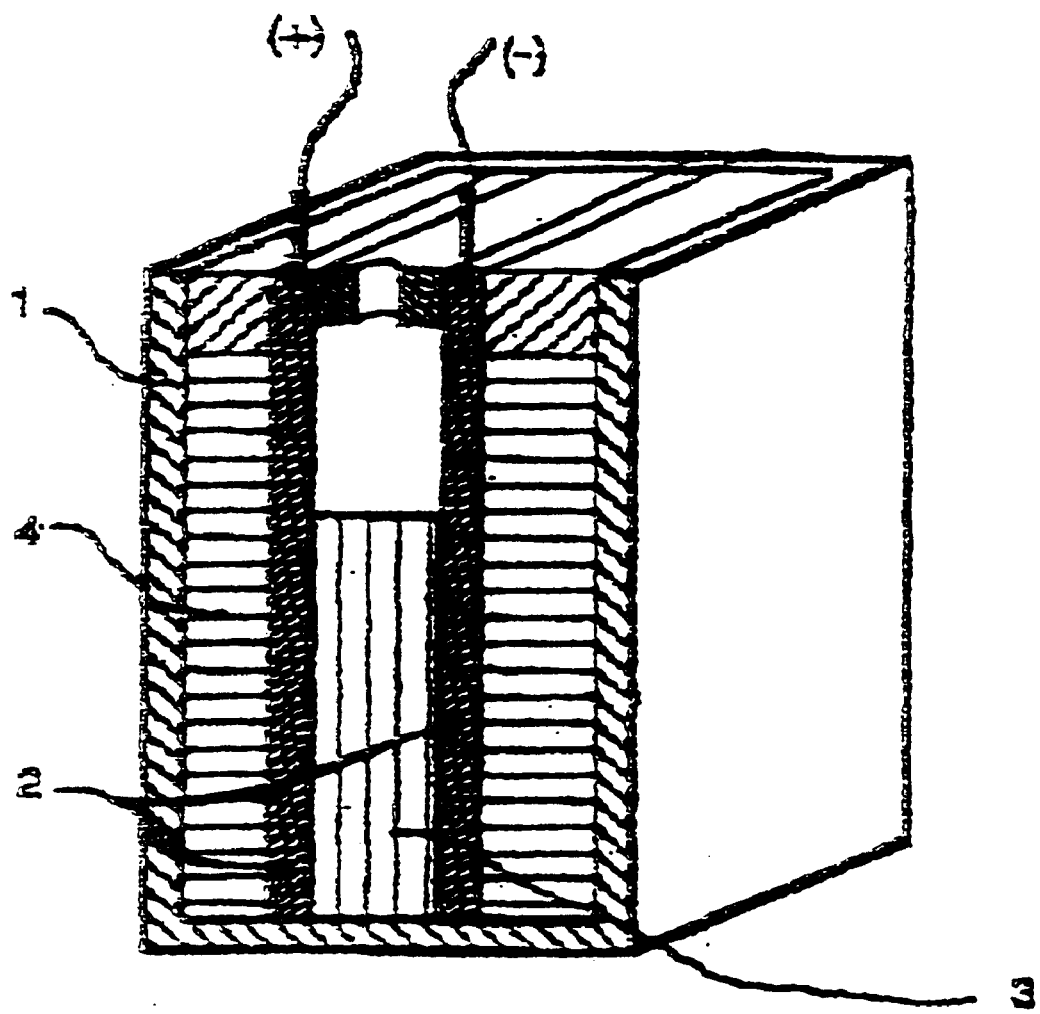
FIG. 1 represents container 1 containing a coating 4 holding the electrodes 2 between which microorganism suspension 3 is introduced.
Figure 3:
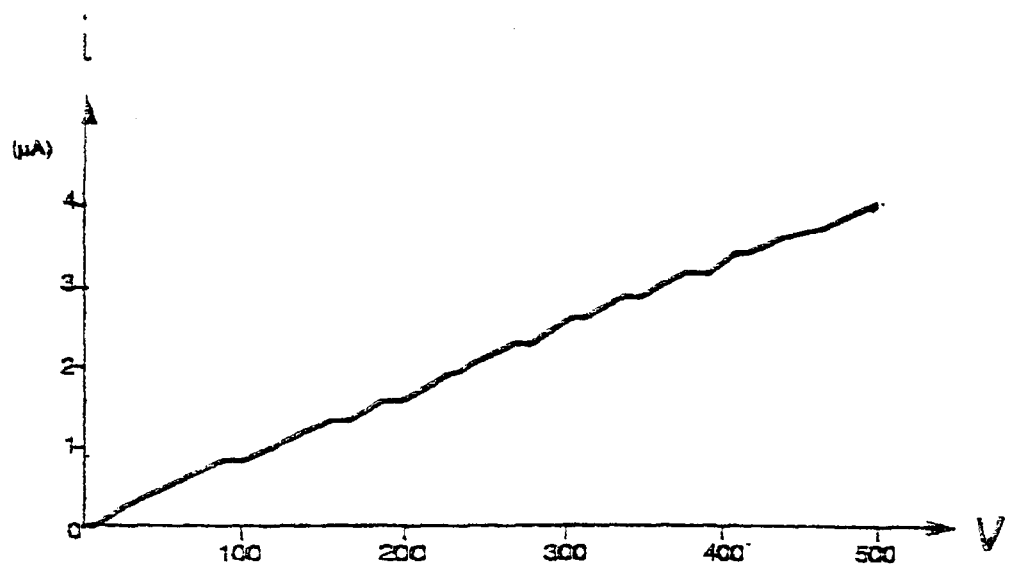
FIG. 3 is a graph of the changes in leakage current as a function of the electrical field applied when the microorganisms are dead.
Figure 4:
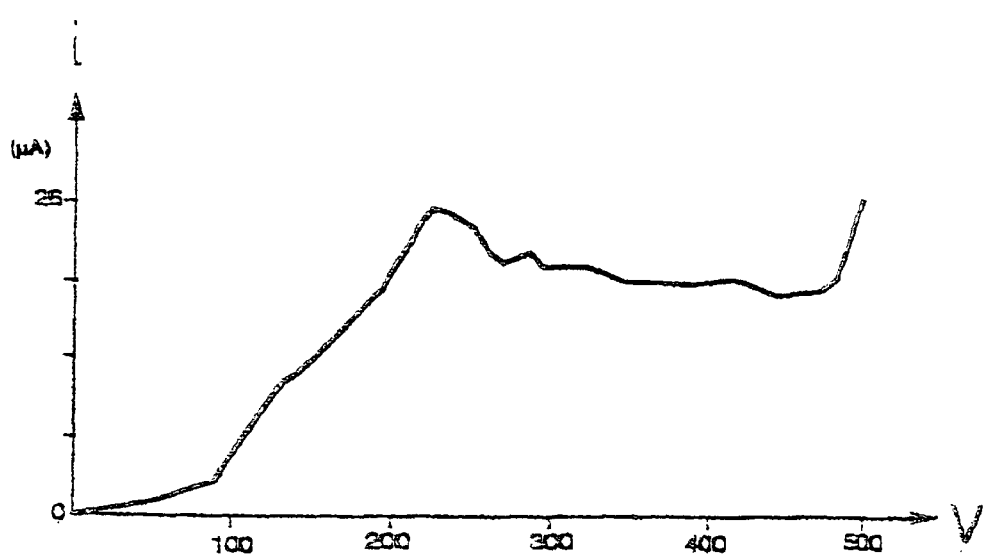
FIG. 4 is a graph of the changes in leakage current strength as a function of the applied electrical field between 0 and 250 V/mm when the microorganisms are alive.
Figure 5:
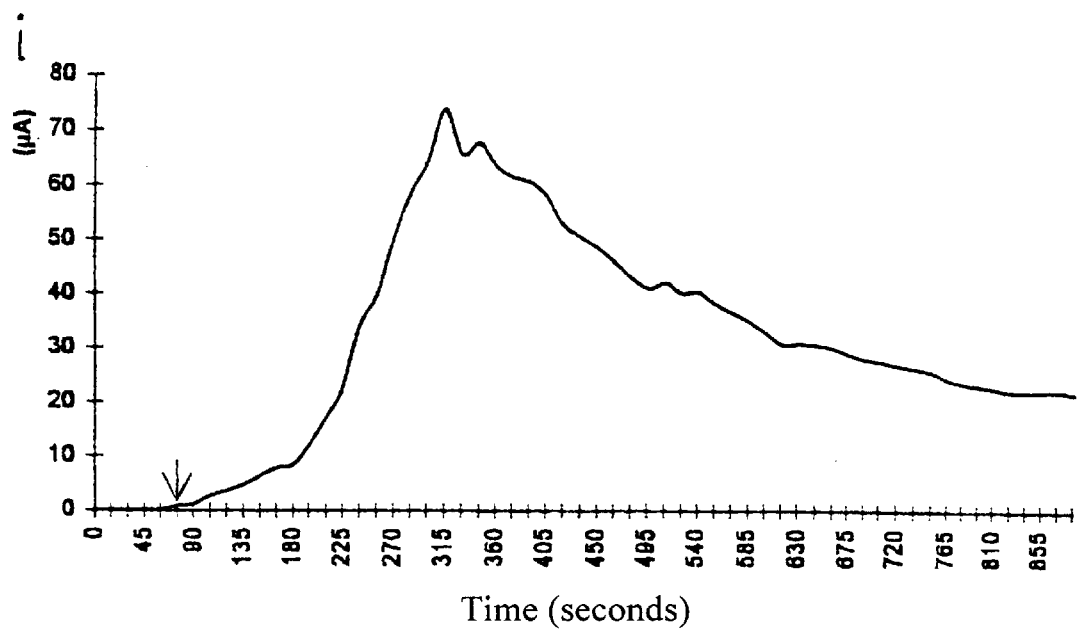
FIG. 5 is a graph of the changes in leakage current strength as a function of time when the voltage is stepped up 2.5 V/mm every 15 seconds up to a final voltage of 25 V/mm marked by the arrow then held at this value.

When the microorganisms are dead, the shape of the curve in FIG. 3 obtained with the device in FIG. 1 is linear. On the other hand, when they are alive, the shape of the curve shown in FIG. 4 and obtained with the device in FIG. 1 is very different: the leakage current increases suddenly for low voltages, peaks at about 220 volts, then drops back suddenly to stabilize at approximately 300 volts.

EXAMPLE 2

The microorganisms studied, coming from an agar culture medium, are scraped off the surface and placed in two Eppendorf microtubes each containing 1 ml of dielectric oil of the silicone oil type. An ultrasound probe is placed in the microtubes, called experimental microtube and control microtube. The ultrasound waves with a power of 25 W and a frequency of 20 kHz are applied to the mixture for 30 seconds alternating with 2 to 3 rest phases lasting 5 seconds each, in order to obtain a homogeneous suspension; any cell aggregates and agar present are centrifuged off at 4000 rpm for 30 seconds at 4° C.

Figure 2:
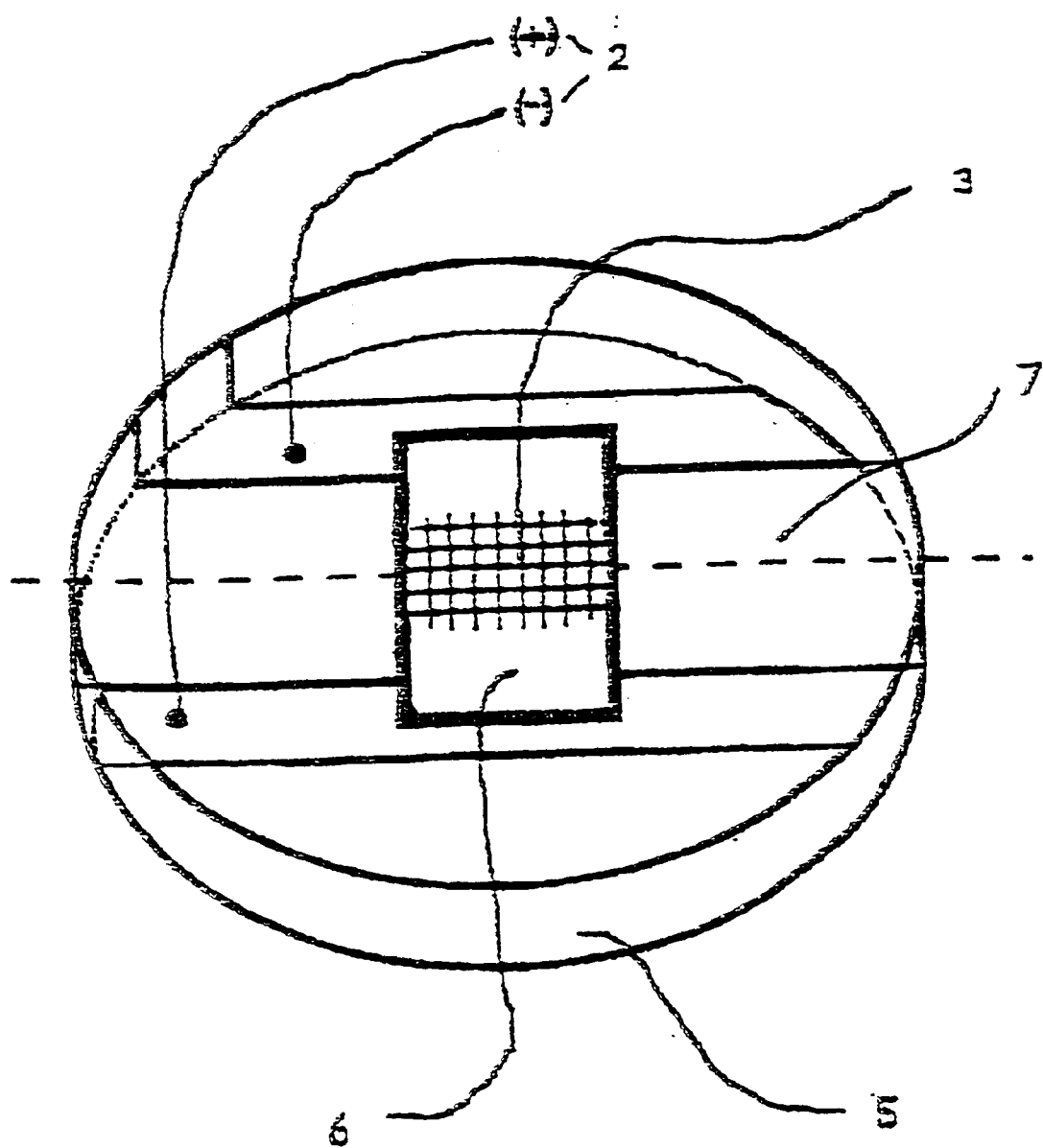
FIG. 2 is a variant of the container comprised of a Petri dish 5 provided with electrodes 2 between which the microorganism suspension 3 is placed on a slide 6 between inter-electrode space 7.

After introduction of the homogenous suspension contained in the experimental microtube into one of the containers shown in FIGS. 1 and 2, the electrical field is applied. Thus, an electrical field with qualitative and quantitative characteristics previously determined according to the type of study conducted and according to the microorganisms studied is applied to one of the suspensions 3 for a given period of time. The medium is transferred to an experimental Eppendorf microtube 2.

The two microtubes are then centrifuged at 10,000 rpm for 30 seconds at 4° C. to recover the solid residues. The silicone oil is removed by inverting the Eppendorf microtubes. 1 ml of 0.05M phosphate buffer solution, pH 7, is added to the control and experimental microtubes 2 and each mixture is homogenized by ultrasound at 25 W, frequency 20 kHz, for 5 seconds. Each suspension is poured into a cotton-plugged tube containing 9 ml of culture medium appropriate for the microorganisms studied.

The bacterial cells are revived after agitation for 3 hours at 150 rpm in the control and experimental cotton-plugged tubes. 1 ml of this first dilution is removed from each tube and transferred to a hemolysis tube to measure the optical density of each cell suspension. A sufficient quantity of 0.05 M phosphate buffer with a pH of 7 is added to the two samples to obtain a final optical density of between 0 and 0.4. Once the optical density of the control and experimental samples are known, the number of cells present in each tube is deduced by comparison with a standard curve obtained using a counting slide to count the number of cells present in each tube.

A dilution series by tens is prepared for each tube. For each dilution, 3 Petri dishes containing agar medium are seeded with 0.1 ml of cell suspension. After 72 hours' incubation at 30° C., the colonies formed on each dish are counted. The percentage of cells alive after application of the electrical field is determined by the ratio between the number of cells present in the experimental tube and the number of cells present in the control tube.

EXAMPLE 3

The procedure is the same as in Example 1.

Figure 6:
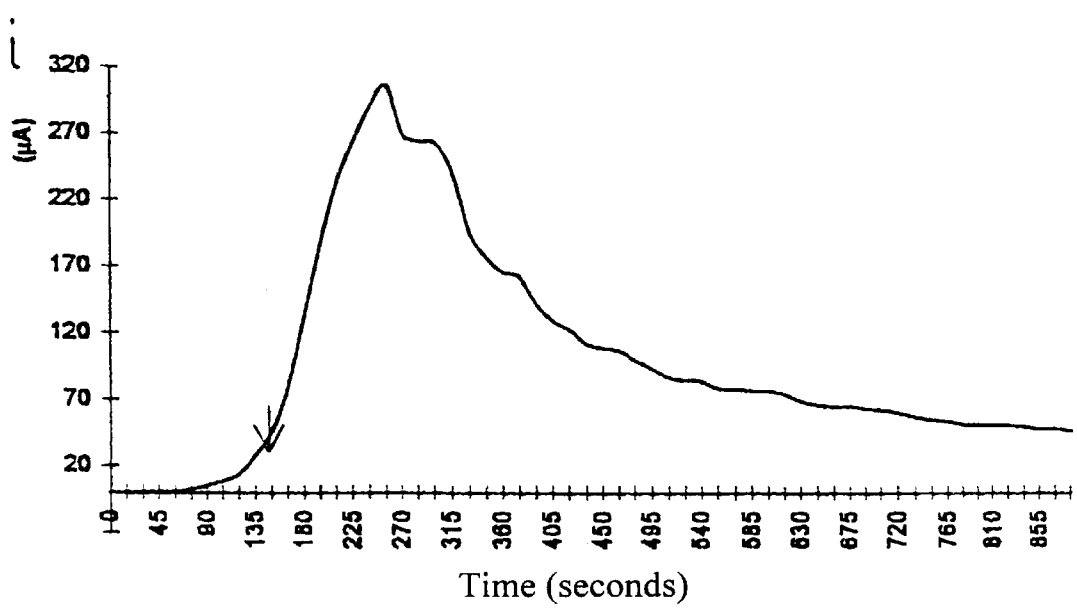
FIG. 6 is a graph of the changes in leakage current strength as a function of time when the voltage is stepped up 5 V/mm every 15 seconds up to a final voltage of 50 V/mm marked by the arrow then held at this value.

The strength of the electrical field applied to suspension 3 is increased in steps of 5 V/mm every 15 seconds until a voltage of 25 V/mm is obtained. The arrow in FIG. 6 shows where the voltage ceases to rise. The time taken for this voltage rise is 1 minute, 15 seconds. The voltage is then held at this value for 13 minutes, 45 seconds so that the experiment lasts a total of 15 minutes. In parallel, an ammeter records the induced leakage current.

As soon as the strength of the electrical field stops increasing, the leakage current rises, first linearly for 100 seconds, then sharply up to a maximum value of over 70 $\mu$A after 330 seconds. For the rest of the time during which the electrical field is applied to cell suspension 3, the leakage current declines to an end value of approximately 20 $\mu$A. The regularity of this decline is interrupted by low-strength secondary peaks.

EXAMPLE 4

The procedure is the same as in Example 1.

Figure 7:
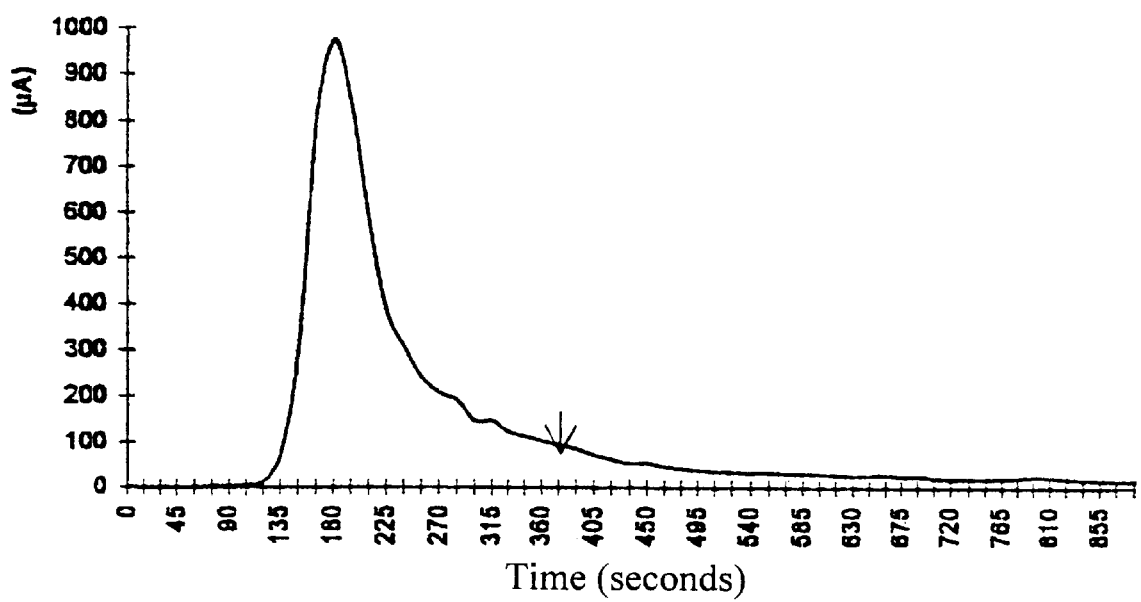
FIG. 7 is a graph of the changes in leakage current strength as a function of time when the voltage is stepped up 10 V/mm every 15 seconds up to a final voltage of 250 V/mm marked by the arrow then held at this value.

The strength of the electrical field applied to suspension 3 is increased in steps of 5 V/mm every 15 seconds until a voltage of 50 V/mm is obtained. The arrow in FIG. 7 shows where the voltage ceases to rise. The time taken for this voltage rise is 2 minutes, 30 seconds. The voltage is then held at this value for 12 minutes, 30 seconds so that the experiment lasts a total of 15 minutes. In parallel, an ammeter records the induced leakage current.

After a slow rise phase in the first minute, the leakage current starts to rise rapidly. This is the beginning of the leakage current peak that occurs after the voltage ceases to rise. The maximum leakage current value recorded after 4 minutes, 30 seconds is 306 $\mu$A. For the rest of the time the electrical field is applied to cell suspension 3, the leakage current strength declines to a final value of approximately 47 $\mu$A. The regularity of this decline is interrupted by low-strength secondary peaks.

EXAMPLE 5

The procedure is the same as in Example 1.

The strength of the electrical field applied to suspension 3 is increased in steps of 10 V/mm every 15 seconds until a voltage of 250 V/mm is obtained. The arrow in FIG. 8 shows where the voltage ceases to rise. The time taken for this voltage rise is 6 minutes, 15 seconds. The voltage is then held at this value for 8 minutes, 45 seconds so that the experiment lasts a total of 15 minutes. In parallel, an ammeter records the induced leakage current.

The leakage current increases slightly for the first two minutes of the voltage rise until the strength of the electrical field reaches 80 V/mm. In the next minute, i.e. between 90 and 130 V/mm, a very sharp rise in leakage current is recorded. After this increase, the value of the leakage current is 97.6 V/mm. The leakage current then decreases almost exponentially until the end of voltage application, reaching an end value of 15 $\mu$A. The regularity of this decline is interrupted by the presence of low-strength secondary peaks.

The method according to the invention enables the status of the bacterial culture to be determined in less than an hour. It obviates expensive handling and involvement of skilled personnel to carry out the visual observations and count the elements cultured in a nutrient medium. Moreover, because the test does not last long, development of contaminants is negligible. Hence it is not necessary to operate in a sterile atmosphere or under conditions of strict asepsis.

Other advantages such as the absence of a specific mediator and the use of classical electrodes enable accurate results to be obtained at low cost.

The method also has the advantage of applying increasing high-strength electrical fields for long periods of time. The measurements made in this way yield results that are consistent and hence more reliably interpreted.

The invention also has the advantage of recovering microorganisms that survive application of the electrical field for possible later use.

What is claimed is:

1. A method for determining the existence of biological activity of microorganisms by applying an electrical field, wherein said method comprises suspension of the microorganisms in a dielectric oil, application of an electrical field to said suspension, and measurement of changes in induced leakage current strength as a function of the electrical field applied.

2. A method according to claim 1, wherein the microorganisms are taken from an agar culture medium.

3. A method according to claim 1, wherein the microorganism suspension is obtained by application of ultrasound to a mixture of dielectric oil and microorganisms.

4. A method according to claim 1, wherein the dielectric oil is a mineral oil or organic oil or a mixture thereof.

5. A method according to claim 4, wherein the dielectric oil is a silicone oil.

6. A device for determining whether microorganisms are biologically active, comprising:
   a container equipped with electrodes in which the microorganism suspension is placed in a dielectric oil;
   means for generating an electric field between two or more electrodes;
   means for measuring induced leakage current; and
   means for recording the induced leakage current.

7. A device according to claim 6, wherein the container into which said suspension is introduced is equipped with metal electrodes.

8. A device according to claim 6, wherein the container into which said suspension is introduced comprises an insulating plate provided with an inter-electrode space.

9. A device according to claim 6, wherein the electrical field between electrodes varies from 0 to 250 volts per millimeter.

10. A method according to claim 1, wherein, after the measurement of the chances in induced leakage current strength, the microorgansims are transferred to an aqueous medium and counted.

* * * * *